United States Patent
Stearns

(10) Patent No.: US 8,094,908 B2
(45) Date of Patent: Jan. 10, 2012

(54) METHOD AND SYSTEM FOR ESTIMATING RANDOMS IN IMAGING DATA

(75) Inventor: Charles William Stearns, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 845 days.

(21) Appl. No.: 12/175,076

(22) Filed: Jul. 17, 2008

(65) Prior Publication Data

US 2010/0014728 A1 Jan. 21, 2010

(51) Int. Cl.
*G06K 9/00* (2006.01)
(52) U.S. Cl. .................... 382/131; 250/363.04
(58) Field of Classification Search .................. 382/128, 382/130–132, 275; 250/362, 363.03, 363.04
See application file for complete search history.

(56) References Cited

U.S. PATENT DOCUMENTS

| | | |
|---|---|---|
| 2005/0129170 A1 | 6/2005 | Watson et al. |
| 2007/0040122 A1 | 2/2007 | Manjeshwar et al. |
| 2007/0106154 A1 | 5/2007 | Conti |

OTHER PUBLICATIONS

Charles W. Stearns; Random Coincidence Estimation from Single Event Rates on the Discovery ST PET/CT Scanner; 0-7803-8258-7/03 (C) 2003 IEEE; 3 pages.

*Primary Examiner* — Courtney Thomas
(74) *Attorney, Agent, or Firm* — Dean D. Small; The Small Patent Law Group

(57) ABSTRACT

A method for estimating randoms in PET imaging data includes acquiring imaging data that includes a plurality of singles and a plurality of randoms, where the randoms exhibit a non-exponential decay, generating a randoms correction estimate based on the non-exponential decay, and applying the randoms correction estimate to the imaging data to generate corrected imaging data. The method further includes generating an image using the corrected image data. An imaging system and computer readable medium programmed to estimate randoms is also provided.

20 Claims, 4 Drawing Sheets

METHOD AND SYSTEM FOR ESTIMATING RANDOMS IN IMAGING DATA

BACKGROUND OF THE INVENTION

This invention relates generally to imaging systems capable of operation in multiple modalities, and more particularly to an apparatus and method for estimating coincidence events generated by a multi-modality imaging system.

Multi-modality imaging systems are capable of scanning using different modalities, such as, for example, Positron Emission Tomography (PET), Single Photon Emission Computed Tomography (SPECT), and Computed Tomography (CT). During operation of a PET imaging system for example, a patient is initially injected with a radiopharmaceutical that emits positrons as the radiopharmaceutical decays. The emitted positrons travel a relatively short distance before the positrons encounter an electron, at which point an annihilation occurs whereby the electron and positron are annihilated and converted into two gamma rays each having an energy of 511 keV.

The annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence, gamma photons also identify a line of response, or LOR, along which the annihilation event has occurred.

The number of time coincidences, generally referred to as coincidence events, detected within a field of view (FOV) of the detector is the count rate of the detector. The count rate at each of two oppositely disposed detectors is generally referred to as singles counts, or singles. The coincidence event is identified if the time difference between the arrivals of signals at the oppositely disposed detectors is less than a predetermined time coincidence. The number of coincidence events per second registered is commonly referred to as prompt coincidences or prompts. Prompts may include true coincidences and random coincidences. True coincidences are those physically correlated time coincidences, i.e., two gamma photons emitted in the process of annihilation or photons produced from the two primary gamma photons.

In addition to the true coincidence events described above, at least one other type of coincidence event, referred to herein as randoms is detected by the PET scanner. The randoms typically confound the data collection and image reconstruction process particularly at high count rates and in volumetric acquisitions. The phenomenon known as randoms occurs when photons from two different annihilations are detected by two crystals at essentially the same time. Randoms are due to valid events being detected at the same time even though the gamma photons did not originate from the same annihilation. The valid events may also come from other non-annihilation sources. These events are called randoms because it is random chance that the two arrived at the same time. The probability of such a random event occurring is directly proportional to the event rate in each of the two single detectors compared in the coincidence pair. Randoms are deleterious to the PET acquisition because, even if the expected number of random coincidences in an acquisition may be estimated and compensated for in the data set, counting the random coincidence events adds Poisson noise to the data set, reducing the signal-to-noise ratio of the data, and, ultimately the reconstructed PET image.

One method to estimate the rate of random coincidence acceptance is referred to as the Randoms from Singles method. The Randoms from Singles method measures the detected singles counts for each channel in the detector and uses those measured counts to predict the random coincidence coincidences for each detector pair in the prompt channel. The conventional Randoms from Singles method relies on the assumption that the singles rate is constant in the detectors for the duration of the acquisition. For example, a constant singles rate is achieved if the activity distribution does not move during the course of the acquisition, and if the acquisition duration is short compared to the half-life of the radiopharmaceutical being imaged. For most radiopharmaceuticals having a relatively long half-life compared to the acquisition interval, the Randoms from Singles method is effective in estimating and eliminating the randoms.

However, if a study is performed using an radiopharmaceutical having a relatively short half-life, the Randoms from Singles method is less effective. For example, if the study is performed using $^{82}Rb^+$, which has a half-life of 1.3 minutes, so that imaging frames of several minutes duration are not short compared to the radiopharmaceutical half-life, then the randoms from singles method may cause quantitative inaccuracies and/or artifacts to occur in the image. In some cases, an assumption of simple exponential decay of the radioisotope in the patient can be used to derive a correction factor for the Randoms from Singles estimate. In other cases, such a model is insufficient, and inaccuracies remain in the Randoms from Singles estimation process. For example, because counts are obviously at a premium in these short scans, these frames may be started while the heart is still taking up activity, so the activity distribution is not stationary even if decay is taken into account. Three-dimensional (3D) image reconstructions may be particularly sensitive to these artifacts, due to the higher fraction of random coincidences in the prompt channel and also the sensitivity of the 3D scatter correction tail fit routine to data which is imprecisely corrected for randoms. However, even in two-dimensional (2D) imaging there is the possibility for quantitative errors to be introduced into the reconstructed images.

BRIEF DESCRIPTION OF THE INVENTION

In one embodiment a method for estimating randoms in PET imaging data is provided. The PET method includes acquiring a plurality of imaging data that includes a plurality of singles and a plurality of randoms at least some of the randoms having a non-exponential decay generating a randoms correction estimate based on the non-exponential decay and applying the randoms correction estimate to the plurality of imaging data to generate corrected imaging data. The method further includes generating an image using the corrected image data.

In another embodiment, a medical imaging system including a computer is provided. The computer is programmed to acquire a plurality of imaging data that includes a plurality of singles and a plurality of randoms at least some of the randoms having a non-exponential decay generate a randoms correction estimate based on the non-exponential decay and apply the randoms correction estimate to the plurality of imaging data to generate corrected imaging data. The computer is also programmed to generate an image using the corrected image data.

In a further embodiment a computer readable medium is provided. The computer readable medium is programmed to instruct a computer to acquire a plurality of imaging data that includes a plurality of singles and a plurality of randoms at least some of the randoms having a non-exponential decay generate a randoms correction estimate based on the non-exponential decay and apply the randoms correction estimate to the plurality of imaging data to generate corrected imaging data. The computer readable medium is also programmed to instruct the computer to generate an image using the corrected image data.

DETAILED DESCRIPTION OF THE INVENTION

Figure 1:
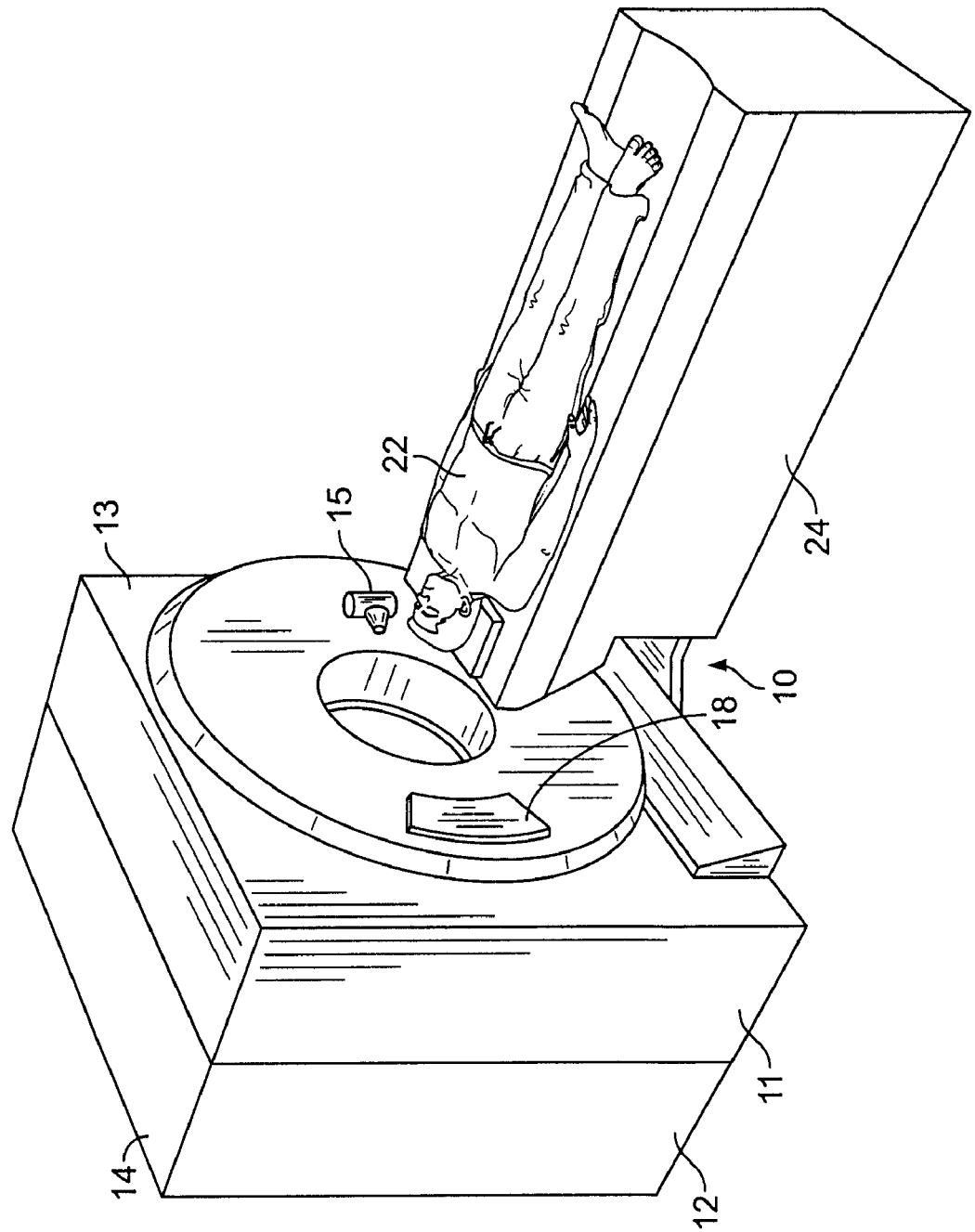
FIG. 1 is a pictorial view of an exemplary multi-modality imaging system in accordance with an embodiment of the present invention.

The foregoing summary as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 2:
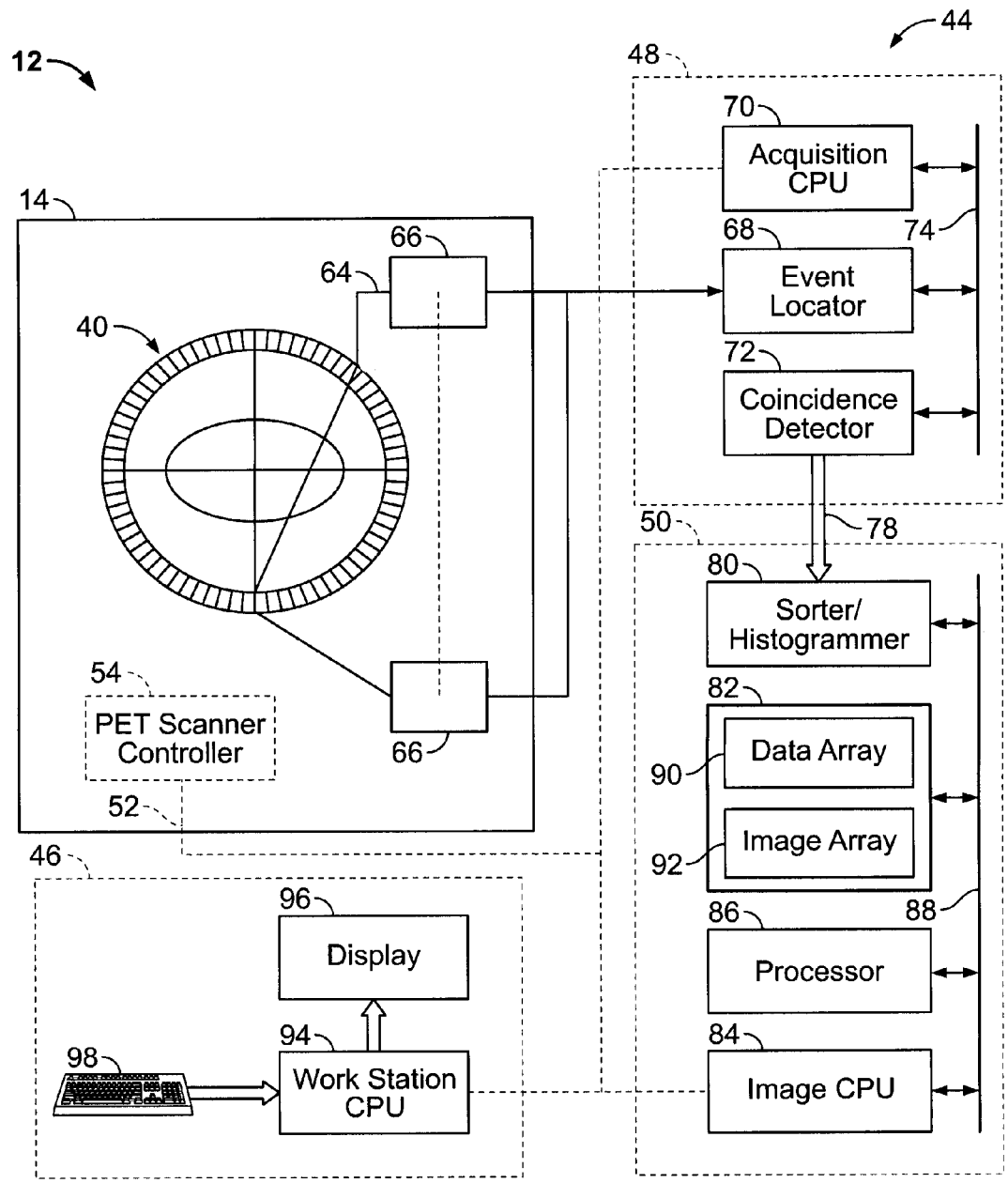
FIG. 2 is a block schematic diagram of the system illustrated in FIG. 1 in accordance with an embodiment of the present invention.

Various embodiments of the invention provide a multi-modality imaging system 10 as shown in FIGS. 1 and 2. Multi-modality imaging system 10 may be any type imaging system for example, different types of medical imaging systems, such as a Positron Emission Tomography (PET), a Single Photon Emission Computed Tomography (SPECT), a Computed Tomography (CT), an ultrasound system Magnetic Resonance Imaging (MRI) or any other system capable or generating tomographic images. The various embodiments are not limited to multi-modality medical imaging systems, but may be used on a single modality medical imaging system such as a stand-along PET imaging system or a stand-along SPECT imaging system for example. Moreover, the various embodiments are not limited to medical imaging systems for imaging human subjects, but may include veterinary or non-medical systems for imaging non-human objects etc.

Referring to FIG. 1, the multi-modality imaging system 10 includes a first modality unit 11 and a second modality unit 12. The two modality units enable the multi-modality imaging system 10 to scan an object or patient in a first modality using the first modality unit 11 and to scan the object or patient in a second modality using the second modality unit 12. The multi-modality imaging system 10 allows for multiple scans in different modalities to facilitate an increased diagnostic capability over single modality systems. In one embodiment, multi-modality imaging system 10 is a Computed Tomography/Positron Emission Tomography (CT/PET) imaging system 10, e.g. the first modality 11 is a CT imaging system 11 and the second modality 12 is a PET imaging system 12. The CT/PET system 10 is shown as including a gantry 13 representative of a CT imaging system and a gantry 14 that is associated with a PET imaging system. As discussed above, modalities other than CT and PET may be employed with the multi-modality imaging system 10.

The gantry 13 includes an x-ray source 15 that projects a beam of x-rays toward a detector array 18 on the opposite side of the gantry 13. Detector array 18 is formed by a plurality of detector rows (not shown) including a plurality of detector elements which together sense the projected x-rays that pass through a medical patient 22. Each detector element produces an electrical signal that represents the intensity of an impinging x-ray beam and hence allows estimation of the attenuation of the beam as it passes through the patient 22. During a scan to acquire x-ray projection data, gantry 13 and the components mounted thereon rotate about a center of rotation.

FIG. 2 is a block schematic diagram of the PET imaging system 12 illustrated in FIG. 1 in accordance with an embodiment of the present invention. The PET imaging system 12 includes a detector ring assembly 40 including a plurality of detector crystals. The PET imaging system 12 also includes a controller or processor 44, to control normalization and image reconstruction processes. Controller 44 is coupled to an operator workstation 46. Controller 44 includes a data acquisition processor 48 and an image reconstruction processor 50, which are interconnected via a communication link 78. PET imaging system 12 acquires scan data and transmits the data to data acquisition processor 48. The scanning operation is controlled from the operator workstation 46. The data acquired by the data acquisition processor 48 is reconstructed using the image reconstruction processor 50.

The detector ring assembly 40 includes a central opening, in which an object or patient, such as patient 22 may be positioned, using, for example, a motorized table 24 (shown in FIG. 1). The motorized table 24 is aligned with the central axis of detector ring assembly 40. This motorized table 24 moves the patient 22 into the central opening of detector ring assembly 40 in response to one or more commands received from the operator workstation 46. A PET scanner controller 54, also referred to as the PET gantry controller, is provided (e.g., mounted) within PET system 12. The PET scanner controller 54 responds to the commands received from the operator workstation 46 through a communication link 52. Therefore, the scanning operation is controlled from the operator workstation 46 through PET scanner controller 54.

Figure 3:
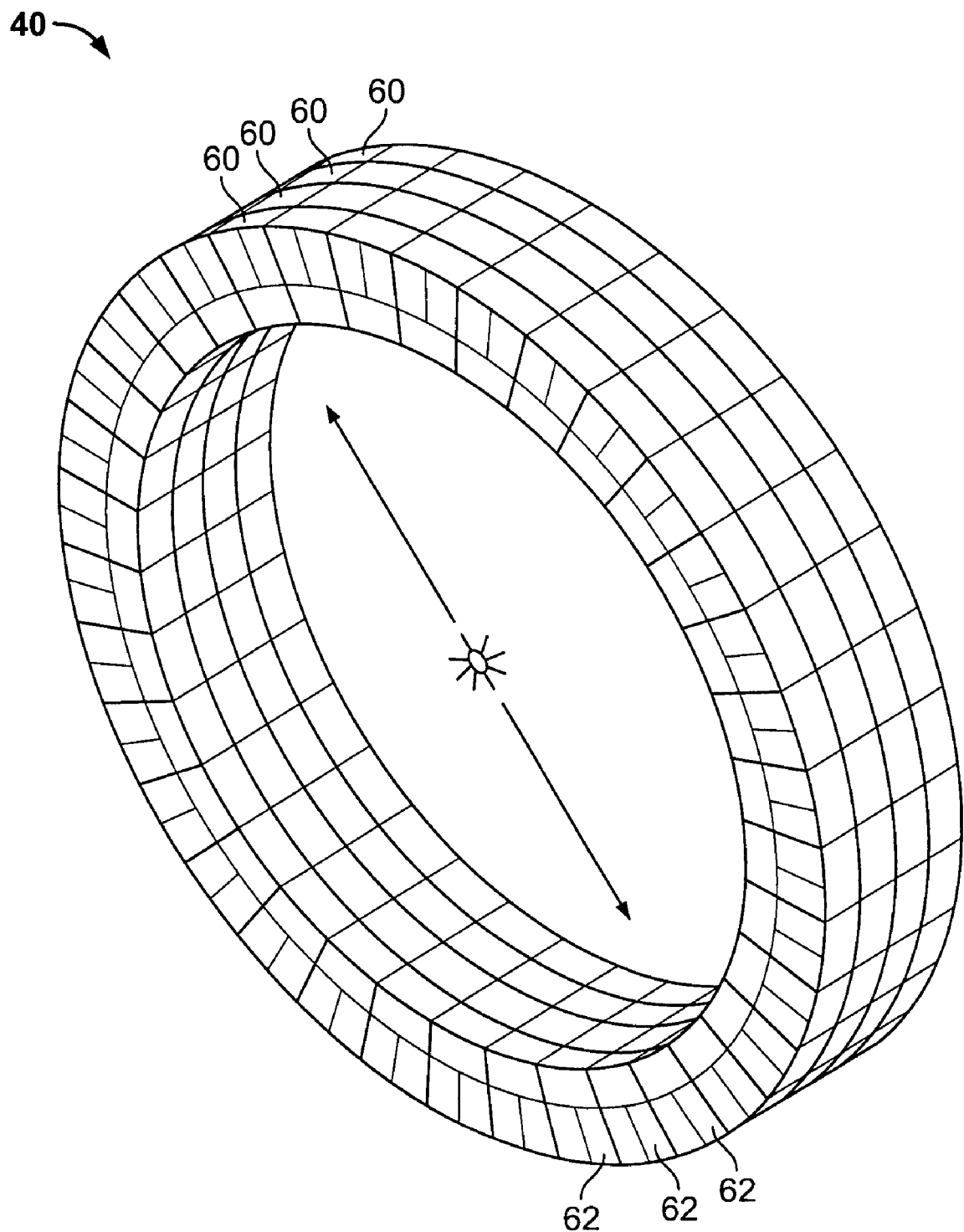
FIG. 3 is a perspective view of the exemplary detector ring assembly shown in FIG. 2 in accordance with an embodiment of the present invention.

FIG. 3 is a perspective view of the exemplary detector ring assembly 40 (shown in FIG. 2). The detector ring assembly 40 includes a plurality of detector rings 60. In the exemplary embodiment detector ring assembly 40 includes twenty-four individual detector rings 60. It should be realized that the quantity of detector rings 60 is exemplary only, and that even though only four detector rings 60 are shown in FIG. 3, the methods described herein may be applied to any exemplary detector ring assembly having N individual detector rings 60, wherein N≧1. Each detector ring 60 also includes M scintillator crystals 62. It should be realized that the quantity of scintillator crystals 62 is exemplary only, and that the methods described herein may be applied to any exemplary detector ring 60 having N individual scintillator crystals 62, wherein M≧2.

Referring again to FIG. 2, during operation, when a photon collides with a crystal 62 on a detector ring 60, the photon collision produces a scintilla on the crystal. Each photomultiplier tube produces an analog signal that is transmitted on communication line 64 when a scintillation event occurs. A set of acquisition circuits 66 is provided to receive these analog signals. Acquisition circuits 66 produce digital signals indicating the 3-dimensional (3D) location and total energy of the event. The acquisition circuits 66 also produce an event detection pulse, which indicates the time or moment the scintillation event occurred. These digital signals are transmitted through a communication link, for example, a cable, to an event locator circuit 68 in the data acquisition processor 48.

The data acquisition processor 48 includes the event locator circuit 68, an acquisition CPU 70 and a coincidence detector 72. The data acquisition processor 48 periodically samples the signals produced by the acquisition circuits 66. The acquisition CPU 70 controls communications on a back-plane bus 74 and on the communication link 78. The event locator circuit 68 processes the information regarding each valid event and provides a set of digital numbers or values indicative of the detected event. For example, this information indicates when the event took place and the position of the scintillation crystal 62 that detected the event. The events are also counted to form a record of the single channel events recorded by each detector element. An event data packet is communicated to the coincidence detector 72 through the back-plane bus 74. The coincidence detector 72 receives the event data packets from the event locator circuit 68 and determines if any two of the detected events are in coincidence. Coincidence is determined by a number of factors. First, the time markers in each event data packet must be within a predetermined time period, for example, 12.5 nanoseconds, of each other. Second, the line-of-response (LOR) formed by a straight line joining the two detectors that detect the coincidence event should pass through the field of view in the PET imaging system 12. Events that cannot be paired are discarded. Coincident event pairs are located and recorded as a coincidence data packet that is communicated through the communication link 78 to a sorter/histogrammer 80 in the image reconstruction processor 50.

During operation, the sorter/histogrammer 80 generates a data structure known as a histogram. A histogram includes a large number of cells, where each cell corresponds to a unique pair of detector crystals in the PET scanner. Because a PET scanner typically includes thousands of detector crystals, the histogram typically includes millions of cells. Each cell of the histogram also stores a count value representing the number of coincidence events detected by the pair of detector crystals for that cell during the scan. At the end of the scan, the data in the histogram is used to reconstruct an image of the patient. The completed histogram containing all the data from the scan is commonly referred to as a "result histogram." The term "histogrammer" generally refers to the components of the scanner, e.g., processor and memory, which carry out the function of creating the histogram.

The image reconstruction processor 50 also includes a memory module 82, an image CPU 84, an array processor 86, and a communication bus 88. During operation, the sorter/histogrammer 80 counts all events occurring along each projection ray and organizes the events into 3D data. This 3D data, or sinograms, is organized in one exemplary embodiment as a data array 90. Data array 90 is stored in the memory module 82. The communication bus 88 is linked to the communication link 78 through the image CPU 84. The image CPU 84 controls communication through communication bus 88. The array processor 86 is also connected to the communication bus 88. The array processor 86 receives data array 90 as an input and reconstructs images in the form of image arrays 92. Resulting image arrays 92 are then stored in memory module 82.

The images stored in the image array 92 are communicated by the image CPU 84 to the operator workstation 46. The operator workstation 46 includes a CPU 94, a display 96 and an input device 98. The CPU 94 connects to communication link 52 and receives inputs, e.g., user commands, from the input device 98. The input device 98 may be, for example, a keyboard, mouse, a touch-screen panel, and/or a voice recognition system etc. Through input device 98 and associated control panel switches, the operator can control the operation of the PET imaging system 12 and the positioning of the patient 22 for a scan. Similarly, the operator can control the display of the resulting image on the display 96 and can perform image-enhancement functions using programs executed by the workstation CPU 94.

Figure 4:
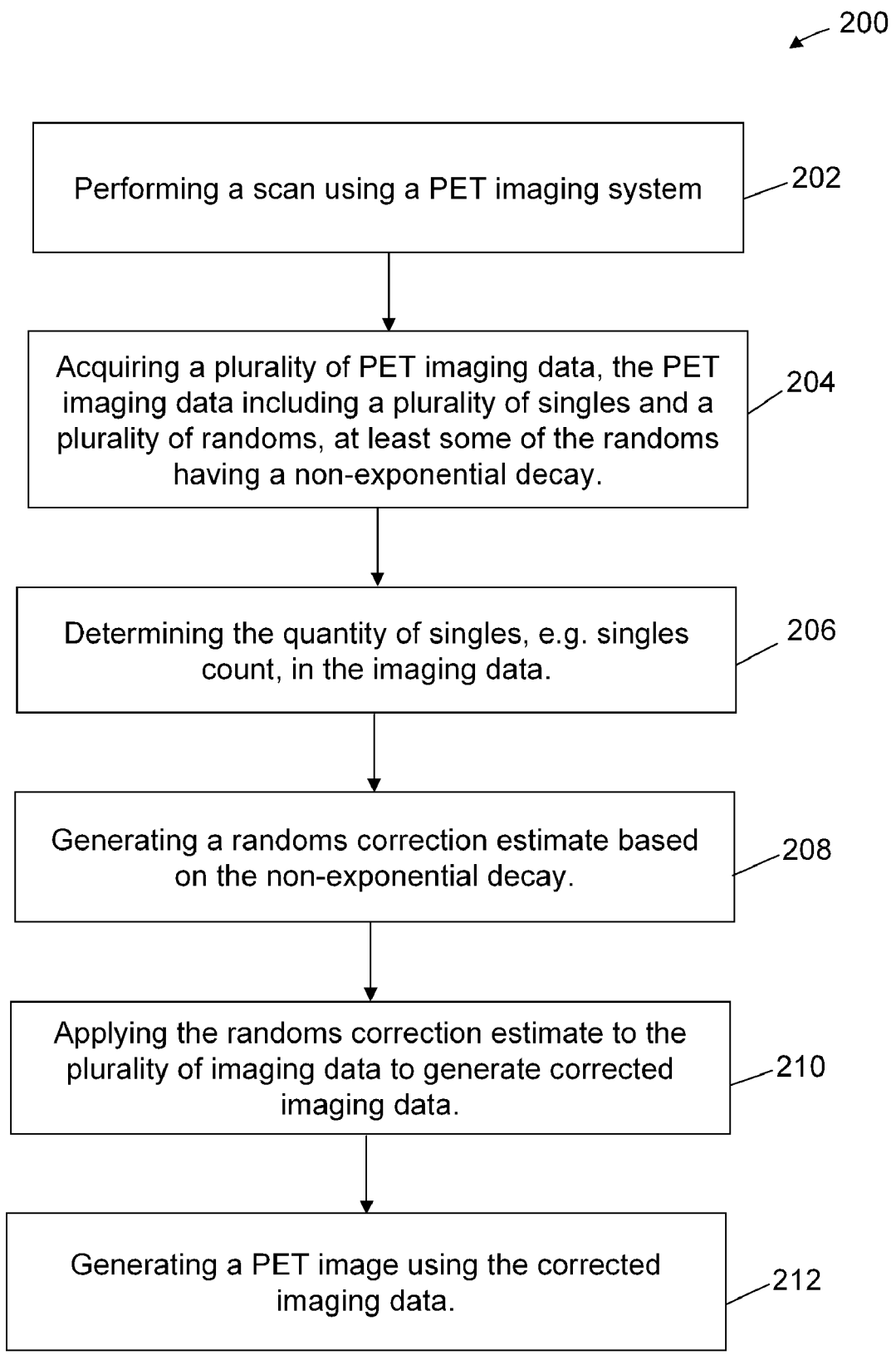
FIG. 4 is a simplified block diagram of an exemplary method performed by the PET imaging system shown in FIG. 2 in accordance with an embodiment of the present invention.

FIG. 4 is a flowchart illustrating an exemplary method of estimating the quantity of randoms in a data imaging stream generated using a PET imaging system. As discussed above, randoms are generated when photons from two different annihilations are detected by two crystals at essentially the same time. Randoms are due to valid events being detected at the same time even though the gamma photons did not originate from the same annihilation.

The method 200 includes performing a scan of a patient using the PET imaging system 12 at step 202. The method 200 also includes acquiring a stream of PET imaging data from the scan at step 204. As discussed above, the imaging data includes both prompt coincidences, which include both trues and randoms and singles. In the exemplary embodiment, the randoms have a non-exponential decay. More specifically during the scanning procedure, the patient is typically injected with a radiopharmaceutical that emits positrons as the radiopharmaceutical decays. In the exemplary embodiment, while the physical decay rate of the radiopharmaceutical is constant, that is the decay rate of the radiopharmaceutical is decreasing at a rate that is proportional to its value, physiological transport of the radiopharmaceutical in to or out of the scanner FOV means that the event rate recorded by the scanner does not exhibit exponential, and a correction term must be applied to the imaging data to estimate the randoms.

To estimate the quantity of randoms having a non-exponential decay the method 200 also includes determining the quantity of singles. e.g. singles counts, in the imaging data at step 206.

In the exemplary embodiment the singles count for each channel in the PET imaging system 12 may be modeled as having the same shape over time in accordance with:

$$s_x(t) = s_x^0 f(t),\quad \text{Equation (1)}$$

where $s_x$ is the singles count for a respective channel or crystal 62 in the detector 40.

In the exemplary embodiment, the total quantity of singles ($S_x$) in a set of imaging data acquired during a single acquisition procedure is then determined or estimated in accordance with:

$$S_x = \int_0^{T_{acq}} s_x(t)\,dt = s_x^0 \int_0^{T_{acq}} f(t)\,dt.\quad \text{Equation (2)}$$

where $T_{acq}$ is the acquisition time to complete the scanning procedure.

The method 200 also includes generating a randoms correction estimate based on the non-exponential decay of the randoms at step 208. In the exemplary embodiment, prior to image reconstruction, the operator enters the radiopharmaceutical used in the scanning procedure into the imaging system 12. In the exemplary embodiment, the imaging system 12 automatically determines the half-life of the radiopharmaceutical and uses the determined half-life to generate the randoms correction estimate. More specifically in one embodiment, the imaging system 12 includes a look-up-table (LUT), or other equivalent program, that includes a variety of radiopharmaceuticals that may be used to perform the scan. The LUT also includes the half-life of each radiopharmaceutical described in the LUT. During operation, the operator may enter the type of radiopharmaceutical used in the scanning procedure, and based on the operator input, system 12 automatically determines the half-life of the radiopharmaceutical and applies the half-life to the equations described herein. Optionally the operator may enter the half-life of the radiopharmaceutical into the imaging system 12.

In the exemplary embodiment, the total random coincidences for the detector pair x-y is therefore in accordance with:

$$\begin{aligned}R_{xy} &= \int_0^{T_{acq}} \tau_{\mathit{eff}}\, s_x(t) s_y(t)\,dt \\ &= \tau_{\mathit{eff}} s_x^0 s_y^0 \int_0^{T_{acq}} f^2(t)\,dt \\ &= \left[ \frac{T_{acq} \int_0^{T_{acq}} f^2(t)\,dt}{\left(\int_0^{T_{acq}} f(t)\,dt\right)^2} \right]\left(\frac{\tau_{\mathit{eff}}}{T_{acq}} S_x S_y\right),\end{aligned}\quad \text{Equation (3)}$$

where $\tau_{\mathit{eff}}$ is effective width of an imaging window;

$s_x s_y$ is the singles count for a respective channel or crystal in an imaging detector;

$S_x S_y$ is the total or average singles count rate in the n'th interval;

$T_{acq}$ is the total acquisition time between 0 and T; and $f(t)$ is a time-varying correction term based on the decay rate of an radiopharmaceutical using in an imaging procedure.

Recognizing the term in parentheses in the last portion of Equation 3 as the Randoms from Singles estimate based on the assumption of constant single channel rates over the course of the acquisition, the portion in square brackets can be considered a correction factor to apply to that inaccurate result, calculated in accordance with $$F = \left[ \frac{T_{acq} \int_0^{T_{acq}} f^2(t)\,dt}{\left(\int_0^{T_{acq}} f(t)\,dt\right)^2} \right]\quad \text{Equation (4)}$$

$T_{acq}$ is the total acquisition time between 0 and T; and $f(t)$ is a time-varying correction term based on the decay rate of an radiopharmaceutical using in an imaging procedure.

In another exemplary embodiment, the integrals in the randoms correction term shown in Equation 4 are computed not from a model of a continuous function $f(t)$ but from a discrete function $S_n$. This function may be determined from sums of the interval-by-interval singles counts in the scanner. Assuming that the acquisition interval is exactly covered by N singles acquisition intervals of equal duration, the correction term is given by:

$$\frac{T_{acq} \int_0^{T_{acq}} f^2(t)\,dt}{\left(\int_0^{T_{acq}} f(t)\,dt\right)^2} = \frac{T_{acq} \sum_n \frac{T_{acq}}{N}\left(\sum_x S_x^n\right)^2}{\left(\sum_n \frac{T_{acq}}{N}\left(\sum_x S_x^n\right)\right)^2}$$

$$= \frac{N \sum_n (\hat{S}_n)^2}{\left(\sum_n \hat{S}_n\right)^2},\quad \text{Equation (5)}$$

where $\hat{S}_n$ is the total (or average) singles count in the n'th interval;

$T_{acq}$ is the total acquisition time between 0 and T; and $f(t)$ is a time-varying correction term based on the decay rate of an radiopharmaceutical using in an imaging procedure;

and N is the total singles counts.

In the exemplary embodiment, the corrected imaging data shown in Equation 5 is then used to generate a PET image using the corrected image data at step 212. More specifically during operation, the PET imaging system 12 generates a plurality of singles and a plurality of randoms where the randoms have a non-exponential decay. A randoms estimate based on the non-exponential decay is generated. In the exemplary embodiment the randoms correction estimate is based on the time-varying non-exponential decay of the randoms $f(t)$. During operation, the integral of the $f^2(t)$ term is generated over a time period between 0 and $T_{acq}$. The $f^2(t)$ term is then divided by the squared integral of the $f(t)$ term to generate the randoms correction estimate shown as Equation 3. Optionally, the randoms correction estimate may be generated by dividing the summation of the squared total (or average) singles count $\hat{S}_n$, in the n'th interval and dividing this summation by the squared summation of the total (or average) singles count $\hat{S}_n$ in the n'th interval, producing a correction term as shown in Equation 5. The randoms correction estimate to the estimated quantity of singles to generate the corrected imaging data.

It should be realized that the correction terms shown in Equations 4 and 5 are exemplary only and that other correction terms may be utilized to correct for randoms occurring in the data. For example, in another exemplary embodiment a correction term may be allocated to the entire task. More specifically, in this embodiment the imaging data may be transmitted to the reconstruction processor 50 and the randoms correction estimates described herein are then performed using the processor 50 using the interval-by-interval singles counts or at least the total counts per interval. In another embodiment, the acquisition portion of imaging system 12, e.g. DAS 48, may be programmed to compute the randoms correction estimate and store the estimate in a rash data file for application by the processor 50 during the image reconstruction process. For example, the DAS 48 may be programmed to automatically compute the correction term from Equation 5 or 6, for example, and multiply each singles count by its square root before storing the singles in the rate data file. The reconstruction processor 50 is then programmed to apply the randoms estimate without modification by multiplying the two square-roots of the correction term together, restoring the correction and effectively computing Equation 6.

At least one technical effect of the methods and apparatus described herein provides the ability to generate a randoms correction factor for imaging data having a non-exponential decay. The randoms correction factors described herein is simpler to calculate and apply than methods. The randoms correction factors described herein are also calculated from data which is easily available in the system. Some embodiments of the present invention provide a machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firm-ware" are interchangeable, and include any computer program stored in memory for execution by a computer, including RAM memory ROM memory EPROM memory EEPROM memory and non-volatile RAM (NVRAM) memory. The above memory types are exemplary only and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for estimating randoms in imaging data comprising:
    acquiring imaging data that includes a plurality of singles and a plurality of randoms where the randoms exhibit a non-exponential decay;
    generating a randoms correction estimate based on the non-exponential decay; and
    applying the randoms correction estimate to the imaging data to generate corrected imaging data.

2. A method in accordance with claim 1 further comprising generating an image using the corrected image data.

3. A method in accordance with claim 1 further comprising generating a randoms correction estimate that is based on the time-varying non-exponential decay of the randoms.

4. A method in accordance with claim 1 further comprising:
receiving an input that is representative of the decay rate of an imaging radiopharmaceutical;
automatically generating a time-varying correction term based on the inputted decay rate; and
generating the randoms correction estimate using the time-varying correction term.

5. A method in accordance with claim 1 wherein generating a randoms correction estimate further comprises:
estimating a quantity of singles in the imaging data; and
applying the randoms correction estimate to the estimated quantity of singles to generate the corrected imaging data.

6. A method in accordance with claim 1 wherein generating a randoms correction estimate further comprises generating a randoms correction estimate in accordance with:

$$\left[ \frac{T_{acq} \int_0^{T_{acq}} f^2(t)\,dt}{\left(\int_0^{T_{acq}} f(t)\,dt\right)^2} \right]$$

where $T_{acq}$ is the total acquisition time between 0 and T; and
$f(t)$ is a time-varying correction term based on the decay rate of an radiopharmaceutical using in an imaging procedure.

7. A method in accordance with claim 1 wherein generating a randoms correction estimate further comprises generating a randoms correction estimate in accordance with:

$$\frac{T_{acq} \int_0^{T_{acq}} f^2(t)\,dt}{\left(\int_0^{T_{acq}} f(t)\,dt\right)^2} = \frac{T_{acq} \sum_n \frac{T_{acq}}{N}\left(\sum_x S_x^n\right)^2}{\left(\sum_n \frac{T_{acq}}{N}\left(\sum_x S_x^n\right)\right)^2}$$

$$= \frac{N \sum_n (\hat{S}_n)^2}{\left(\sum_n \hat{S}_n\right)^2}$$

where $T_{acq}$ is the total acquisition time between 0 and T;
$S_n$ is the total or average singles count rate in the n'th interval; and
N is the total number of intervals.

8. A method in accordance with claim 1 wherein generating a randoms correction estimate further comprises generating a randoms correction estimate ($R_{xy}$) in accordance with:

$$R_{xy} = \int_0^{T_{acq}} \tau_{eff} s_x(t) s_y(t)\,dt$$

$$= \tau_{eff} s_x^0 s_y^0 \int_0^{T_{acq}} f^2(t)\,dt$$

$$= \left(\frac{\tau_{eff}}{T_{acq}} S_x S_y\right) \left[\frac{T_{acq} \int_0^{T_{acq}} f^2(t)\,dt}{\left(\int_0^{T_{acq}} f(t)\,dt\right)^2}\right]$$

where $\tau_{eff}$ is effective width of an imaging window;
$s_x, s_y$ is the singles count for a respective channel or crystal in an imaging detector;
$S_x, S_y, S_n$ is the total or average singles count rate in the n'th interval;
$T_{acq}$ is the total acquisition time between 0 and T; and
$f(t)$ is a time-varying correction term based on the decay rate of an radiopharmaceutical using in an imaging procedure.

9. A medical imaging system comprising:
a detector array; and
a computer operationally coupled to the detector array wherein the computer is programmed to:
acquire imaging data that includes a plurality of singles and a plurality of randoms where the randoms exhibit a non-exponential decay;
generate a randoms correction estimate based on the non-exponential decay; and
apply the randoms correction estimate to the imaging data to generate corrected imaging data.

10. A medical imaging system in accordance with claim 9, wherein said detector array comprises a Positron Emission Tomography (PET) detector, said imaging data comprises a stream of PET imaging data, and said computer comprises a coincidence processor module.

11. A medical imaging system in accordance with claim 9 wherein said computer is further programmed to generate a PET image using the corrected image data.

12. A medical imaging system in accordance with claim 9 wherein said computer is further programmed generate a randoms correction estimate that is based on the time-varying non-exponential decay of the randoms.

13. A medical imaging system in accordance with claim 9 wherein said computer is further programmed to:
receive an input that is representative of the decay rate of an imaging radiopharmaceutical;
automatically generate a time-varying correction term based on the inputted decay rate; and
automatically generate the randoms correction estimate using the time-varying correction term.

14. A medical imaging system in accordance with claim 9 wherein said computer is further programmed to:
estimate a quantity of singles in the imaging data; and
apply the randoms correction estimate to the estimated quantity of singles to generate the corrected imaging data.

15. A medical imaging system in accordance with claim 9 wherein said computer is further programmed to generate a randoms correction estimate in accordance with:

$$\left[ \frac{T_{acq} \int_0^{T_{acq}} f^2(t)\,dt}{\left(\int_0^{T_{acq}} f(t)\,dt\right)^2} \right]$$

where $T_{acq}$ is the total acquisition time between 0 and T; and
$f(t)$ is a time-varying correction term based on the decay rate of an radiopharmaceutical using in an imaging procedure.

16. A medical imaging system in accordance with claim 9 wherein said computer is further programmed to generate a randoms correction estimate in accordance with:

$$\frac{T_{acq} \int_0^{T_{acq}} f^2(t)dt}{\left(\int_0^{T_{acq}} f(t)dt\right)^2} = \frac{T_{acq} \sum_n \frac{T_{acq}}{N}\left(\sum_x S_x^n\right)^2}{\left(\sum_n \frac{T_{acq}}{N}\left(\sum_x S_x^n\right)\right)^2}$$

$$= \frac{N \sum_n (\hat{S}_n)^2}{\left(\sum_n \hat{S}_n\right)^2}$$

where $T_{acq}$ is the total acquisition time between 0 and T;
$S_n$ is the total or average singles count rate in the n'th interval; and
N is the total number of intervals.

17. A medical imaging system in accordance with claim 9 wherein said computer is further programmed to generate a randoms correction estimate ($R_{xy}$) in accordance with:

$$R_{xy} = \int_0^{T_{acq}} \tau_{eff} s_x(t) s_y(t) dt$$

$$= \tau_{eff} s_x^0 s_y^0 \int_0^{T_{acq}} f^2(t) dt$$

$$= \left(\frac{\tau_{eff}}{T_{acq}} S_x S_y\right) \left[\frac{T_{acq} \int_0^{T_{acq}} f^2(t)dt}{\left(\int_0^{T_{acq}} f(t)dt\right)^2}\right]$$

where $\tau_{eff}$ is effective width of an imaging window;
$s_x, s_y$ is the singles count for a respective channel or crystal in an imaging detector;
$S_x, S_y, S_n$ is the total or average singles count rate in the n'th interval;
$T_{acq}$ is the total acquisition time between 0 and T; and
$f(t)$ is a time-varying correction term based on the decay rate of an radiopharmaceutical using in an imaging procedure.

18. A computer readable medium encoded with a program programmed to instruct a computer to:

acquire imaging data that includes a plurality of singles and a plurality of randoms where the randoms exhibit a non-exponential decay;
generate a randoms correction estimate based on the non-exponential decay; and
apply the randoms correction estimate to the imaging data to generate corrected imaging data.

19. A computer readable medium in accordance with claim 18, said computer readable medium is further programmed to instruct a computer to generate a randoms correction estimate in accordance with:

$$\left[\frac{T_{acq} \int_0^{T_{acq}} f^2(t)dt}{\left(\int_0^{T_{acq}} f(t)dt\right)^2}\right]$$

where $T_{acq}$ is the total acquisition time between 0 and T; and
$f(t)$ is a time-varying correction term based on the decay rate of an radiopharmaceutical using in an imaging procedure.

20. A computer readable medium in accordance with claim 18, said computer readable medium is further programmed to instruct a computer to generate a randoms correction estimate in accordance with:

$$\frac{T_{acq} \int_0^{T_{acq}} f^2(t)dt}{\left(\int_0^{T_{acq}} f(t)dt\right)^2} = \frac{T_{acq} \sum_n \frac{T_{acq}}{N}\left(\sum_x S_x^n\right)^2}{\left(\sum_n \frac{T_{acq}}{N}\left(\sum_x S_x^n\right)\right)^2}$$

$$= \frac{N \sum_n (\hat{S}_n)^2}{\left(\sum_n \hat{S}_n\right)^2}$$

where $T_{acq}$ is the total acquisition time between 0 and T;
$S_n$ is the total or average singles count rate in the n'th interval; and
N is the total number of intervals.

* * * * *